(12) United States Patent
Take

(10) Patent No.: US 7,035,447 B2
(45) Date of Patent: Apr. 25, 2006

(54) SEMICONDUCTOR WAFER EXAMINATION SYSTEM

(75) Inventor: Kunihiko Take, Kanagawa (JP)

(73) Assignee: Sony Corporation, Tokyo (JP)

( * ) Notice: Subject to any disclaimer, the term of this patent is extended or adjusted under 35 U.S.C. 154(b) by 484 days.

(21) Appl. No.: 09/732,393

(22) Filed: Dec. 7, 2000

(65) Prior Publication Data
US 2003/0164942 A1 Sep. 4, 2003

(30) Foreign Application Priority Data
Dec. 7, 1999 (JP) ............................... P11-348080

(51) Int. Cl.
G06K 9/00 (2006.01)
(52) U.S. Cl. ...................... 382/145; 382/382; 382/224
(58) Field of Classification Search ............... 382/141, 382/145, 149, 150, 190, 209, 224; 348/125, 348/126, 128–130; 356/237.2–237.5; 345/700
See application file for complete search history.

(56) References Cited
U.S. PATENT DOCUMENTS

| | | | |
|---|---|---|---|
| 6,185,324 B1 * | 2/2001 | Ishihara et al. | 382/149 |
| 6,233,719 B1 * | 5/2001 | Hardikar et al. | 716/1 |
| 6,292,582 B1 * | 9/2001 | Lin et al. | 382/149 |
| 6,438,438 B1 * | 8/2002 | Takagi et al. | 700/121 |

* cited by examiner

Primary Examiner—Vikkram Bali
(74) Attorney, Agent, or Firm—Sonnenschein, Nath & Rosenthal LLP

(57) ABSTRACT

A semiconductor wafer examination system can accurately and reliably detects defects of semiconductor wafers. The semiconductor wafer examination system 1 comprises a defect classification device for automatically classifying defects of semiconductor wafers on the basis of defect detection parameters and a knowledge base and a classification support device for supporting the operation of the defect classification device. The defect detection parameters define the permissible deviation of the surface image of a defective semiconductor wafer from that of a normal semiconductor wafer. The knowledge base contains data for the types of defects that can occur in semiconductor wafers and data for showing the characteristics of each type. The classification support device prepares data on isolated defective areas that are used for selecting and/or altering the defect detection parameters and preparing the knowledge base.

1 Claim, 7 Drawing Sheets

SEMICONDUCTOR WAFER EXAMINATION SYSTEM

RELATED APPLICATION DATA

The present application claims priority to Japanese Application No. P11-348080 filed Dec. 7, 1999, which application is incorporated herein by reference to the extent permitted by law.

BACKGROUND OF THE INVENTION

1. Field of the Invention

This invention relates to an examination system to be used for examining semiconductor wafers.

2. Related Background Art

A semiconductor device is prepared by forming an exquisitely fine device pattern on a semiconductor wafer. When forming a device pattern, particles of dirt can adhere to the surface of the semiconductor wafer and/or the wafer can be damaged to make the wafer defective. A semiconductor device formed on such a defective wafer is a defective device that reduces the overall yield of manufacturing semiconductor devices.

Therefore, to hold the yield of the manufacturing line to a high level, defects caused by dirt and damages have to be detected in earlier stages and the causes of the defects should be identified so that effective counter measures may be taken for the manufacturing facility and the manufacturing process.

It is a common practice that, when a defect is detected, it is examined by means of an examination device to identify the type of the defect and also the facility and the process that produced the defect. The examination device for examining the type of the defect is typically an optical microscope that produces an magnified image of the defect to make it possible to identify the type of the defect.

In order to improve the manufacturing facility and the manufacturing process on the basis of the detected defects, it is desirable to examine semiconductor wafers as many as possible for defects and pin-spot the right causes of the detected defects. However, as device rules are downsized for semiconductor wafers, there arise a variety of defects to make it difficult to visually identify defects in a short period of time. To cope with this problem, there have been proposed automatic defect classification systems adapted to pick up an image of the surface of a semiconductor wafer and automatically determine the type of the defects found on the semiconductor wafer on the basis of the picked up image.

However, known automatic defect classification systems need improvements for more accurately identifying the type of each defect found on a semiconductor wafer.

BRIEF SUMMARY OF THE INVENTION

Under these circumstances, it is therefore the object of the present invention to provide a semiconductor wafer examination system that can detect the defects of a semiconductor wafer more accurately than ever.

According to the invention, the above object is achieved by providing a semiconductor wafer examination system comprising a defect classification device and a classification support device.

The defect classification device is adapted to pick up an image of the surface (defect image) of a defective semiconductor wafer, compare the defect image with an image of the surface of a normal semiconductor wafer (normal image), identify each defective area isolated as characteristic area of a defect in the defect image on the basis of the outcome of the comparison and defect detection parameters for defining threshold values for defects and automatically determine the type of defect of the defective area on the basis of a knowledge base for determining the type of defect according to the characteristic quantity of the defective area.

The classification support device comprises a classification means for identifying the defective areas of a plurality of defect images on the basis of the normal image and the defect detection parameters and classifying the identified defective areas; a defective area display means for displaying the plurality of defective areas as classified by said classification means, an editing means for editing the defect detection parameters on the basis of the defective areas displayed by said defective area display means, a classification result re-instructing means for manually re-classifying the result of classification of the defective areas obtained by said classification means and a selection means for selecting classified defect image data for preparing the knowledge base from the plurality of defective areas as classified by the classification result re-instructing means.

In the semiconductor wafer examination system, the defect classification device and the classification support device are separated from each other. The defect classification device determines the type of defect of each defective semiconductor wafer on the basis of the defect detection parameters and the knowledge base, whereas the classification support device selects and alters defect detection parameters and prepares data on the isolated defective areas for the purpose of preparing the knowledge base.

With this arrangement, a semiconductor wafer examination system according to the invention can accurately and reliably detect defects of semiconductors. Additionally, a semiconductor wafer examination system according to the invention is a highly efficient system due to the fact that it comprises a defect classification device and a classification support device and can carry out the operation of selecting and altering defect detection parameters and preparing data on isolated defective areas for the purpose of preparing a knowledge base independently from the operation of classifying defects to improve the efficiency of the operation.

DETAILED DESCRIPTION OF THE INVENTION

Now, the present invention will be described by referring to the accompanying drawing that illustrate a preferred embodiment of semiconductor wafer examination system according to the invention (to be referred to simply as examination system hereinafter).

Figure 1:
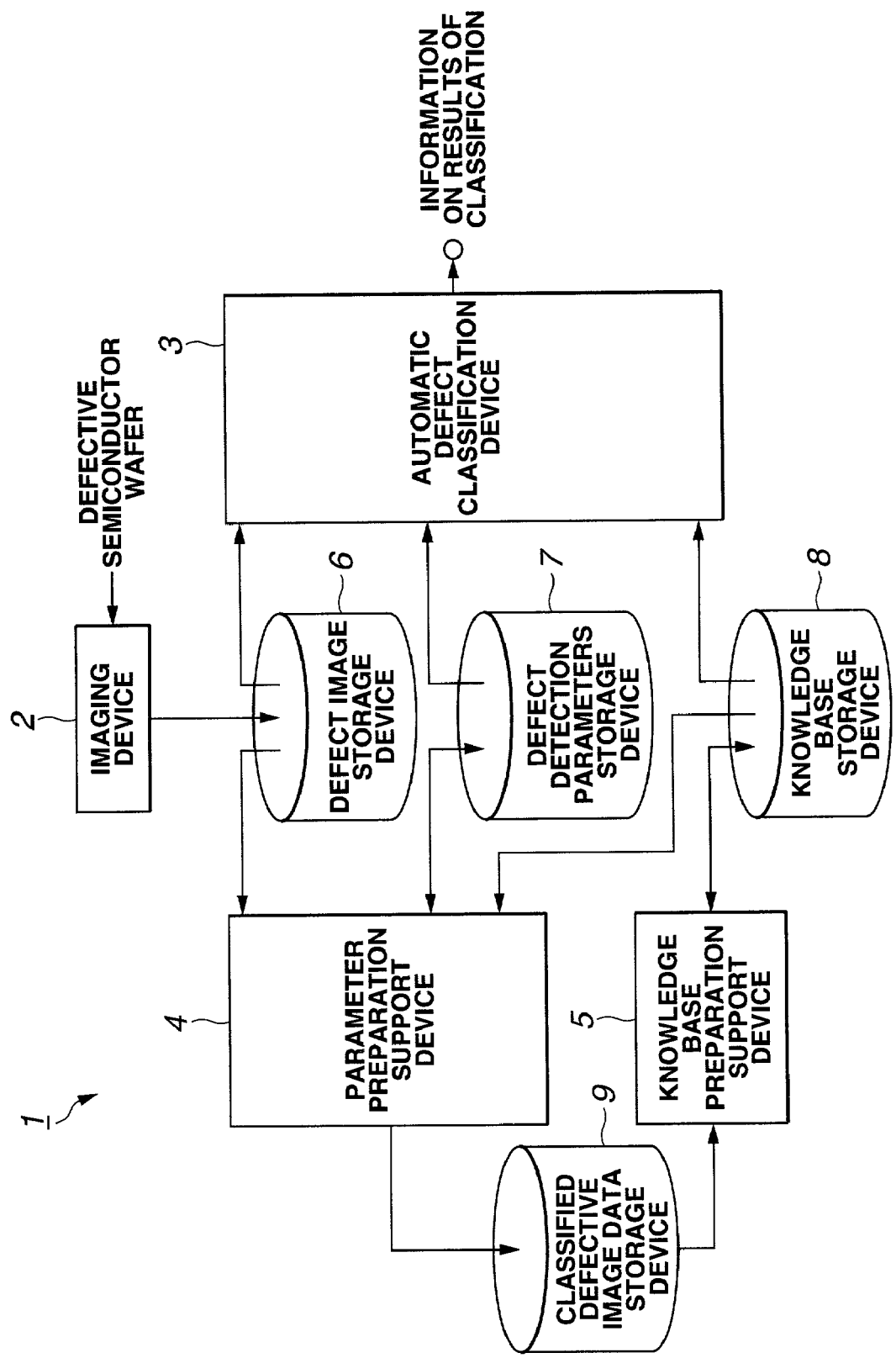
FIG. 1 is a schematic block diagram of an embodiment of semiconductor wafer examination system according to the invention.

FIG. 1 is a schematic block diagram of the embodiment of semiconductor wafer examination system according to the invention.

The examination system 1 of FIG. 1 comprises an imaging device 2, an automatic defect classification device 3, a parameter preparation support device 4, a knowledge base preparation support device 5, a defect image storage device 6, a defect detection parameters storage device 7, a knowledge base storage device 8 and a classified defect image data storage device 9.

This examination system 1 has a function of examining the defects produced on semiconductor wafer and automatically classifying the types of the defects and a function of supporting the automatic defect classifying function. Of the examination system 1, the imaging device 2 and the automatic defect classification device 3 are responsible to the automatic defect classifying function, while the parameter preparation support device 4 and the knowledge base preparation support device 5 are responsible to the support function. Normally, only the automatic defect classifying function is used in the process of examining semiconductors.

The imaging device 2 has a stage for supporting a semiconductor wafer, an illumination optical system for irradiating the semiconductor wafer supported by the stage with light, a detection optical system for enlarging the image formed by the light reflected from the irradiated semiconductor wafer by means of an objective lens and an imaging section such as a CCD for picking up a magnified image of the semiconductor wafer detected by the detection optical system. The imaging device 2 is adapted to obtain defect image data by picking up a magnified image of the defective areas of the surface of the semiconductor wafer and store the obtained defect image data in the defect image storage device 6.

The automatic defect classification device 3 automatically analyses the defect image data obtained from the image picked up by the imaging device 2 and classifies each of the defects of the semiconductor wafer by type. Types of defects that are used by the automatic defect classification device 3 for classification include scar, dirt, extra pattern and missing pattern. The automatic defect classification device 3 performs the classifying operation by using the defect detection parameters stored in the defect detection parameters storage device 7 and the knowledge base stored in the knowledge base storage device 8.

For the purpose of the invention, defect detection parameters are used for defining threshold values for permitting (or rejecting) surface images of defective semiconductor wafers. When classifying defect images, the automatic defect classification device 3 determines the difference between the image of each defective circuit pattern and that of the normal circuit pattern of the same circuit and isolate the defective areas of the picked up defect image. Since an image normally contains noise and imaging shears, not only defective areas but also non-defective areas may show differences. Therefore, the automatic defect classification device 3 should be so adapted that it isolates only those areas whose images that are different from the normal image greater by such an extent that is greater than a predetermined value and the defect detection parameters are used for defining threshold values for the difference and other necessary values.

More specifically, defect detection parameters include one for defining the permissible deviation from normal for defects, one for determining if the pattern of a defect image agrees with that of a normal image or not, a maximal value for the possibility of positional discrepancy of a defect image from a normal image and one for the information for specifying a region from which noise should be eliminated.

The knowledge base contains data for the types of defects that can occur in semiconductor wafers and data for showing the characteristics of each type. Data for showing the characteristics of each type are not data on defect images but characteristic quantities of each aspect of the type when defect images of the type are analysed in that aspect. The characteristic quantities may include those that represent the size of defect, the density of defects (when a plurality of defects are found densely), the sharpness of the boundary of a defective area, the roundness of defect, the smoothness of the edges of defect, the brightness of defect and so on.

The automatic defect classification device 3 analyses each image that shows a defective area and is isolated by using the above described defect detection parameters. Then, it compares the result of the analysis with the corresponding data of the knowledge base and determines the type of the defect of the defective area and hence that of the defects appearing the in the semiconductor wafer.

Thus, the automatic defect classification device 3 classifies the defects of each defect image stored in the defect image storage device 6 and outputs the results of the classification to the user.

The parameter preparation support device 4 selects and/or alters the defect detection parameters to be used by the automatic defect classification device 3 to classify each defect image. The parameter preparation support device 4 also prepares classified defect image data to be used for preparing the knowledge base. Note that the knowledge base preparation support device 5 is responsible for the operation of preparing and altering the knowledge base. The parameter preparation support device 4 prepares defect detection parameters and classified defect image data, using the defect image data stored in the defect image storage device 6, the defect detection parameters stored in the defect detection parameters storage device 7 and the knowledge base stored in the knowledge base storage device 8.

For the purpose of the invention, classified defect image data are those showing the characteristic quantities of the image data obtained when a defective area is isolated from a defect image. The operation of isolating a defect area is carried out by using defect detection parameters. The parameter preparation support device 4 transforms the image data of the isolated defect area into characteristic quantities of different aspects of defect including the size of defect, the density of defects (when a plurality of defects are found densely), the sharpness of the boundary of a defective area, the roundness of defect, the smoothness of the edges of defect, the brightness of defect and so on and then generates classified defect image data. The generated classified defect image data are used for preparing the knowledge base and represent a defect image selected out of a plurality of defect images of the defect type as one that best shows the characteristics of the defect type.

The parameter preparation support device 4 stores the selected and/or altered defect detection parameters in the defect detection parameters storage device 7 and the prepared classified defect image data in the classified defective image data storage device 9.

The knowledge base preparation support device 5 prepares and/or alters the knowledge base on the basis of the classified defect image data stored in the classified defective image data storage device 9. The knowledge base preparation support device 5 analyses the classified defect image data supplied as data showing characteristic quantities of image data and selectively transforms some of them into data of the knowledge base. The obtained data of the knowledge base are then stored in the knowledge base storage device 8.

Figure 2:
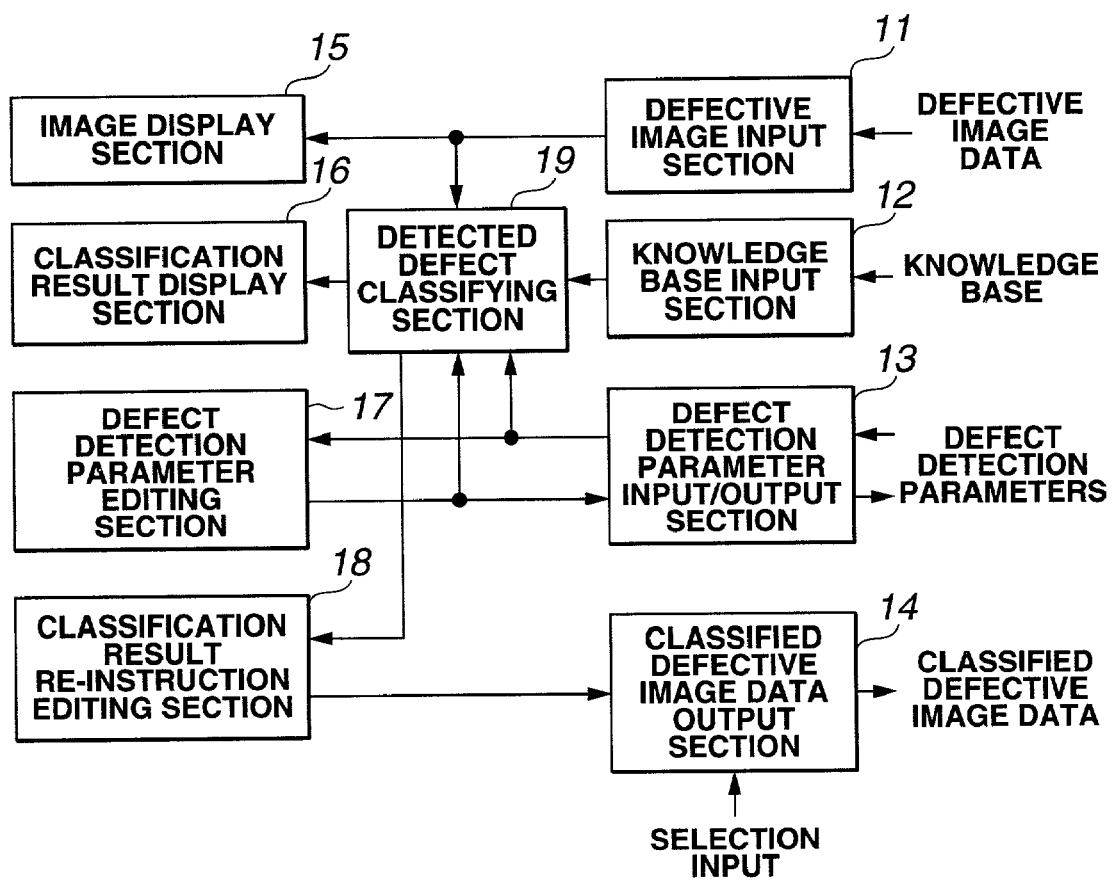
FIG. 2 is a schematic block diagram of the parameter preparation support device of the examination system of FIG. 1.

Now, the parameter preparation support device 4 will be described in greater detail by referring to FIG. 2.

The parameter preparation support device 4 has a defect image input section 11, a knowledge base input section 12, a defect detection parameter input/output section 13, a classified defect image data output section 14, an image display section 15, a classification result display section 16, a defect detection parameter editing section 17, a classification result re-instruction editing section 18 and a detected defect classifying section detected defect classifying section 19.

The defect image input section 11 reads out the defect image data stored in the defect image storage device 6. The defect image input section 11 then supplies the obtained defect image data to the image display section 15 or the detected defect classifying section 19.

The knowledge base input section 12 reads out the knowledge base stored in the knowledge base storage device 8. Then, the knowledge base input section 12 stores the knowledge base read by it in the detected defect classifying section 19. While the knowledge base is also read out for automatic classifying operation of the detected defect classifying section 19, it does not need to be read out for manual classifying operation.

The defect detection parameter input/output section 13 reads out the defect detection parameters stored in the defect detection parameters storage device 7. Then, the defect detection parameter input/output section 13 supplies the defect detection parameters read out by it to the defect detection parameter editing section 17 and the detected defect classifying section 19. If no defect detection parameter is selected nor stored in the defect detection parameters storage device 7, the defect detection parameter input/output section 13 does not read out any defect detection parameter. The defect detection parameter input/output section 13 writes the defect detection parameters selected and/or altered by the defect detection parameter editing section 17 in the defect detection parameters storage device 7.

The classified defect image data output section 14 stores the classified defect image data about which the result of classification is re-instructed by the classification result re-instruction editing section 18 in the classified defective image data storage device 9. At this time, the classified defect image data output section 14 receives the selection input of the user and stores only the classified defect image data selected by the selection input in the classified defective image data storage device 9.

The image display section 15 displays the defect image data fed from the defect image input section 11.

The classification result display section 16 displays the classified defect image data obtained as a result of the processing and detecting operations of the detected defect classifying section 19.

When the detected defect classifying section 19 carries out processing and detecting operations, the defect detection parameter editing section 17 performs the editing operation of selecting and/or altering defect detection parameters according to the user operation. The edited defect detection parameters are then fed to the detected defect classifying section 19 and the defect detection parameter input/output section 13.

If the result of classification obtained by the detected defect classifying section 19 on the basis of the known knowledge base is wrong or the detected data cannot be automatically classified by the detected defect classifying section 19 because it does not read any knowledge base, the classification result re-instruction editing section 18 re-classifies the result of classification according to the user operation. The re-classified defect image data are supplied to the classified defect image data output section 14.

The detected defect classifying section 19 isolates each defective area from the input defect image data, using the defect detection parameters, and classifies the image of the isolated defect in terms of types of defects.

When the detected defect classifying section 19 is isolating a defective area, the user judges if the state of isolation of the defective area isolated by using defect detection parameters is precisely correct or not by referring to the defect image displayed on the image display section 15 and, if wrong, the defect detection parameter editing section 17 alters or reselects the defect detection parameters. When the reselected defect detection parameters are confirmed, they are used as right defect detection parameters.

When the detected defect classifying section 19 classifies the data of the defective area isolated from the defect image data, the user judges the type of each defect by referring to the image of the detected defect as displayed on the classification result display section 16 so that the defect is manually classified by way of the classification result re-instruction editing section 18. The classifying operation may be carried out automatically by using the knowledge base if the knowledge base is already stored in the knowledge base storage device 8. If such is the case, the user judges if the classifying operation of the classification result re-instruction editing section 18 is correct or not and, if the classification is found to be wrong, the classification result re-instruction editing section 18 issues a re-instruction for the classifying operation.

The parameter preparation support device 4 having the above described configuration operates in a manner as described below.

Firstly, the defect image input section 11 reads out the defect image data of a large number of defect images, which may be 100 to 1,000 images, from the defect image storage device 6 as sample data. The read out defect image data of the large number of defect images are used by the detected defect classifying section 19 for isolating and classifying each defect. The details of the defect detection parameters selected for the operation of isolating defects are regulated by the user. If any of the defect detection parameters is altered by the user, the detected defect classifying section 19 carries out the operation of isolating the corresponding defects for another time and the defect detection parameter input/output section 13 stores the altered defect detection parameters in the defect detection parameters storage device 7. Each of the defect images is also classified by the user. The number of classified defect image data obtained as a result of the classifying operation is equal to that of the input samples. Then, the user selects only the classified defect image date that he or she deems necessary, typically including those that show the characteristics of the defects and hence suitably be used for preparing the knowledge base, and then stores the selected classified defect image data in the classified defective image data storage device 9.

Now, the operation of the parameter preparation support device 4 that is performed in response to the input operation of the user will be described by referring to the flow charts of the accompanying drawing.

Figure 3:
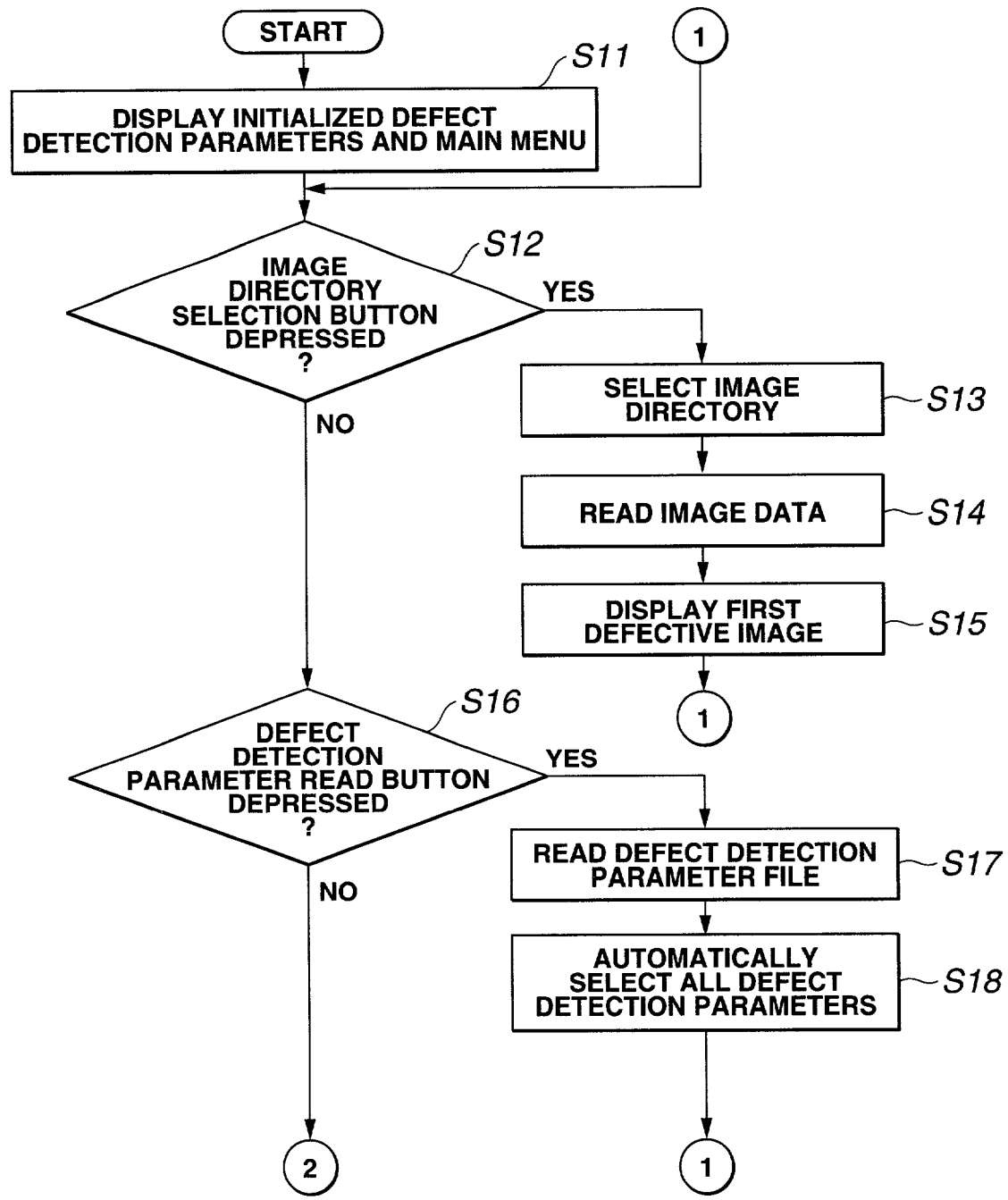
FIG. 3 is a flow chart of the processing operation of the parameter preparation support device of FIG. 2.

To begin with, the monitor screen of the parameter preparation support device 4 displays the main menus as user interface, which main menu contains the following buttons. As any of the buttons is selected and depressed by the user, the parameter preparation support device 4 carries out the operation corresponding to the depressed button.

image directory selection button
    defect detection parameter read button
    individual defect detection parameter manual selection button
    defect detection parameter preservation button
    knowledge base read button
    classified defect image data file name selection button
    classified defect image data preservation button
    classification result instruction selection button
    detected defect classification start button
    next defect image display button
    previous defect image display button
    defect image display button
    reference image display button
    detected defect image display button Referring to FIG. 3, as power is input or an application program is started, the parameter preparation support device parameter preparation support device 4 initializes the defect detection parameters and displays the main menu (Step S11).

Then, as the image directory selection button is depressed (Step S12), an image directory storing defect image data is selected (Step S13) and the defect image data of the selected image directory are read out from the defect image storage device 6 (Step S14) so that the initial defect image data are displayed (Step S15). As the initial defect image data are displayed, the operation returns to the main menu.

Then, if the defect detection parameter read button is depressed (Step S16), the defect detection parameters are read out from the defect detection parameters storage device 7 (Step S17) and values are automatically selected for all the defect detection parameters (Step S18). As values are automatically selected for all the defect detection parameters, the operation returns to the main menu.

Figure 4:
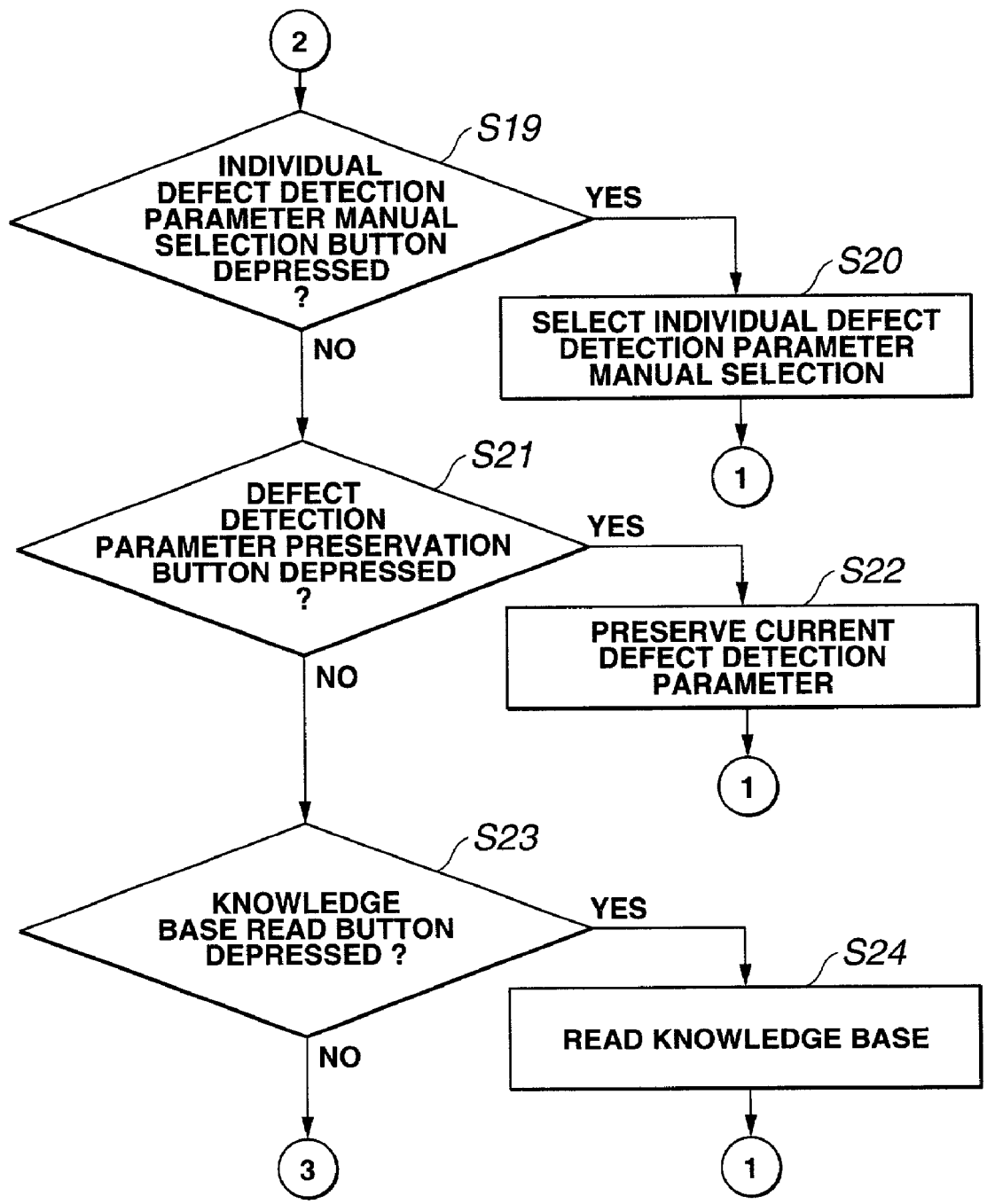
FIG. 4 is a flow chart of the processing operation of the parameter preparation support device of FIG. 2, showing the steps following those of FIG. 3.

Thereafter, referring to FIG. 4, if the individual defect detection parameter manual selection button is depressed (Step S19), the display screen shows the individual defect detection parameters so that values may be selected for them by the user (Step S20). The defect detection parameters include one for defining the permissible deviation from the image of a normal semiconductor wafer in terms of defects, one for determining if the pattern of a defect image agrees with that of a normal image or not, a maximal value for the possibility of positional discrepancy of a defect image from a normal image and one for the information for specifying a region from which noise should be eliminated and the user select a value for each of them. As values are selected for the individual defect detection parameters, the operation returns to main menu.

Then, if the defect detection parameter preservation button is depressed (Step S21), the currently selected values of the defect detection parameters are stored in the defect detection parameters storage device 7 (Step S22). As the current values of the defect detection parameters are preserved, the operation returns to the main menu.

Subsequently, if the knowledge base read button is depressed (Step S23), the knowledge base is read out from the knowledge base storage device 8 (Step S24). As the knowledge base is read out, the operation returns to the main menu.

Figure 5:
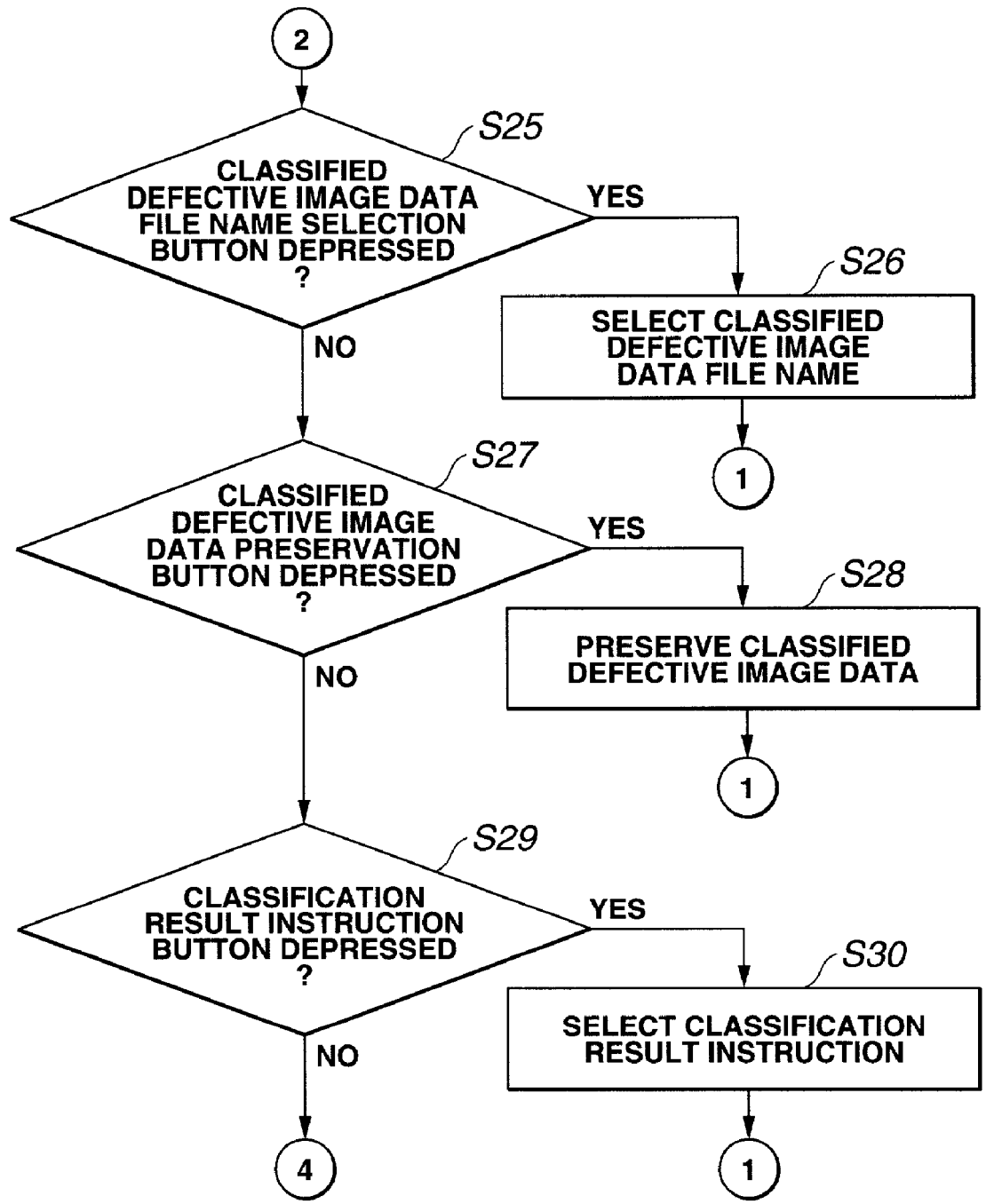
FIG. 5 is a flow chart of the processing operation of the parameter preparation support device of FIG. 2, showing the steps following those of FIG. 4.

Then, referring to FIG. 5, if the classified defect image data file name selection button is depressed (Step S25), the display screen shows classified defect image data file names from which user selects a specific file name (Step S26). As a classified defect image data file name is selected, the operation returns to the main menu.

Thereafter, if the classified defect image data preservation button is depressed (Step S27), the classified defect image data are stored in the classified defective image data storage device 9 (Step S28). As the classified defect image data are preserved, the operation returns to main menu.

Then, if the classification result instruction selection button is depressed (Step S29), the classified defect image data that are classified according to the types of defects are displayed on the classification result display section 16 and an instruction for the classified result is selected (Step S30). As the instruction for the classified result is selected, the operation returns to the main menu.

Figure 6:
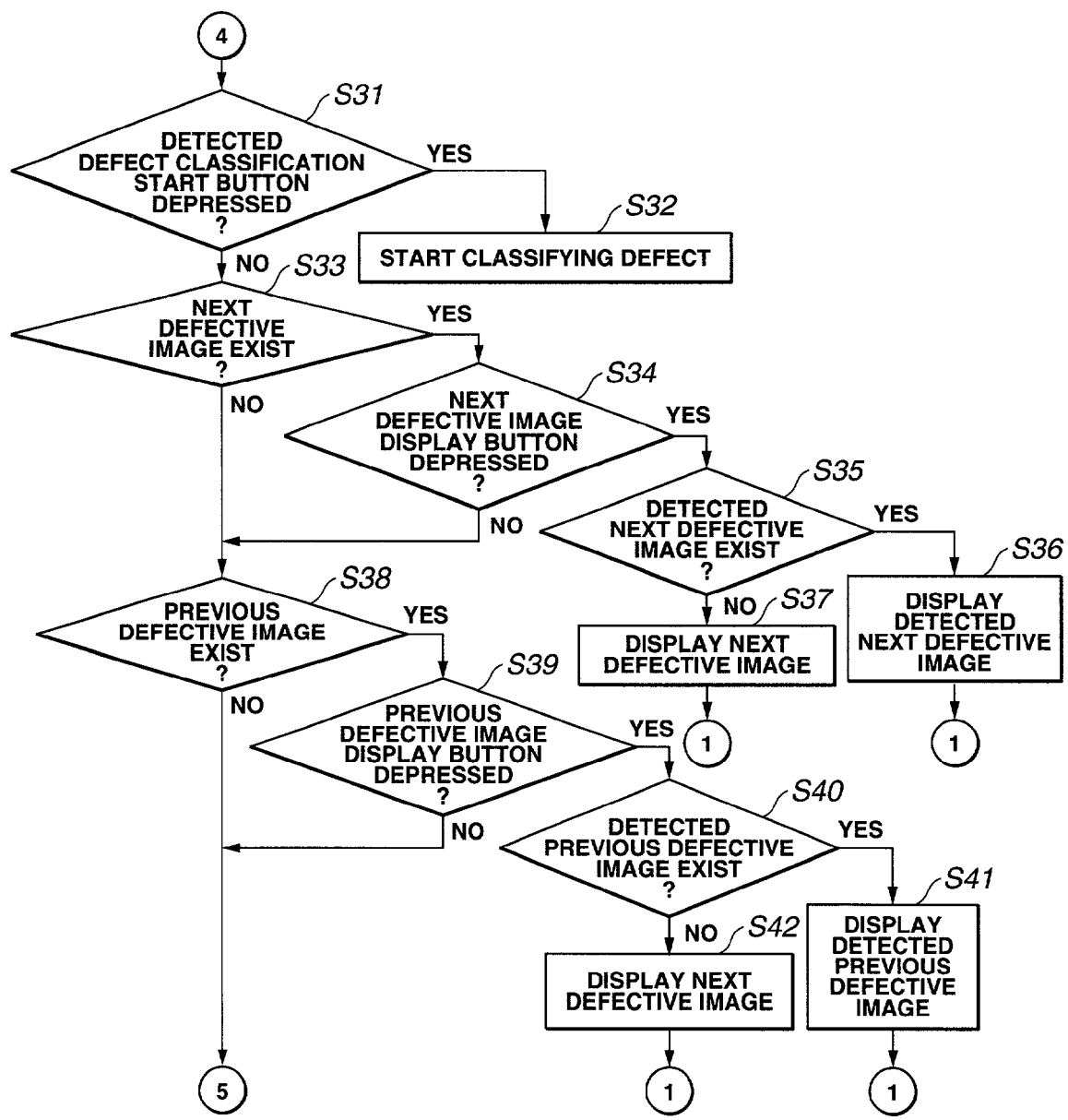
FIG. 6 is a flow chart of the processing operation of the parameter preparation support device of FIG. 2, showing the steps following those of FIG. 5.

Subsequently, referring to FIG. 6, if the detected defect classification start button is depressed (Step S31), an operation of classifying the detected defects starts (Step S32). As the classification is terminated, the operation returns to the main menu.

If, on the other hand, the detected defect classification start button is not depressed, it is determined if there is any defect image that needs to be classified (Step S33). If it is determined that there is a defect image that needs to be classified and the next defect image display button is depressed (Step S34), it is determined if there exists the next detected defect image or not (Step S35). If it is determined that there exists the next detected defect image, the detected defect image is displayed on the image display section 15 (Step S36). If, on the other hand, it is determined that there does not exist the next detected defect image, the after the next detected defect image is displayed on the image display section 15 (Step S37). After terminating Steps S36 and S37, the operation returns to the main menu.

If it is determined in Step S33 that there does not exist any detected defect image to be classified or in Step S34 that the next defect image display button is not depressed, it is determined if there exists any previously classified defect image (Step S38). If it is determined that there exits a previously classified defect image and the previous defect image display button is depressed (Step S39), it is determined if there exists any image that has previously been detected for defects or not (Step S40). If it is determined that there exists an image that has previously been detected for defects, the detected defect image is displayed on the image display section 15 (Step S41). If, on the other hand, it is determined that there does not exist any image that has previously been detected for defects, the next defect image is displayed on the image display section 15 (Step S42). After terminating Steps S41 and S42, the operation returns to the main menu.

Figure 7:
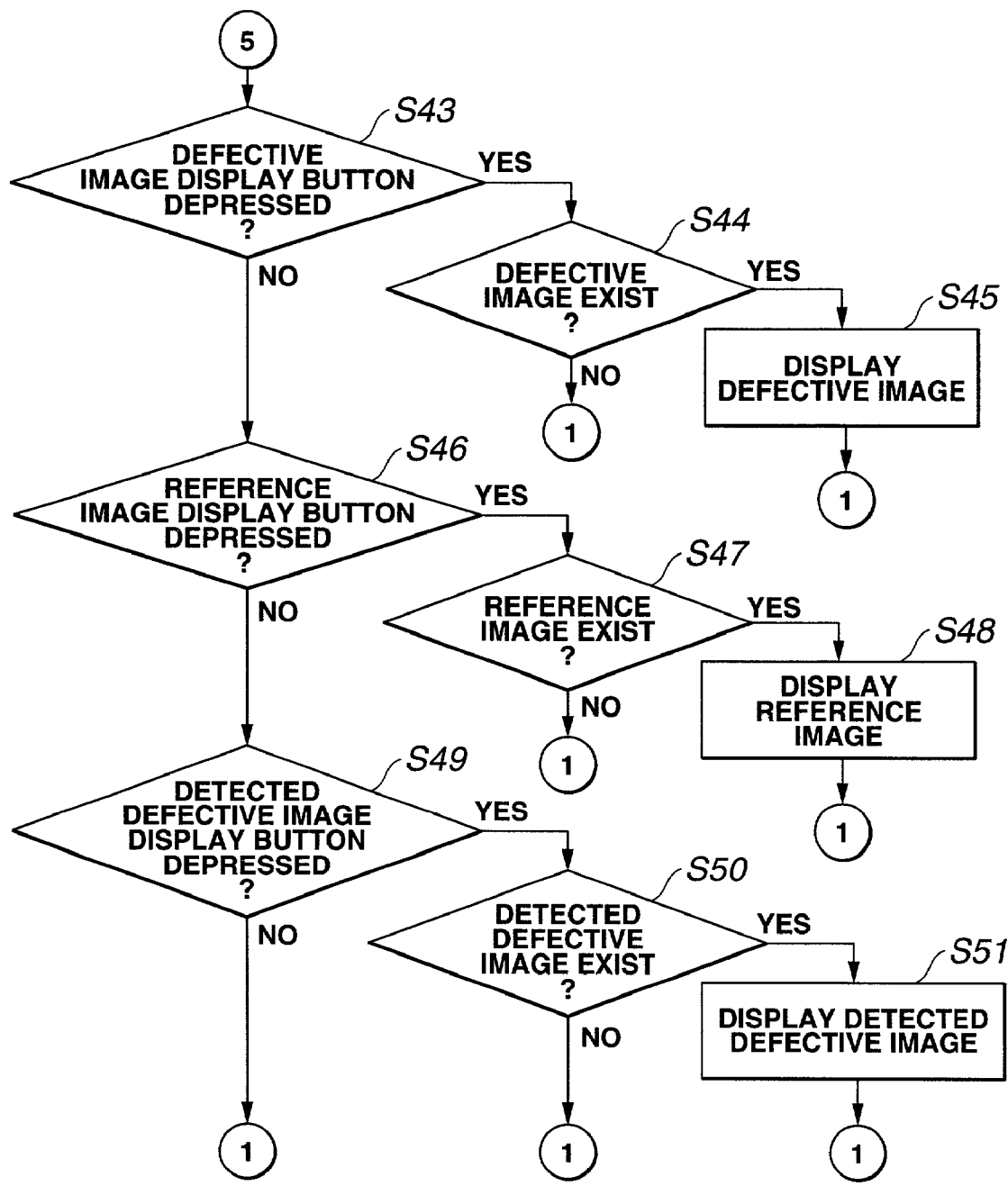
FIG. 7 is a flow chart of the processing operation of the parameter preparation support device of FIG. 2, showing the steps following those of FIG. 6.

Then, referring to FIG. 7, if the defect image display button is depressed (Step S43), it is determined if there is any defect image or not (Step S44). If it is determined that there is a defect image, it is displayed on the image display section 15 (Step S45). As the defect image is displayed, the operation returns to the main menu.

Thereafter, if the reference image display button is depressed (Step S46), it is determined if there is any reference image or not (Step S47). If it is determined that there is a reference image, it is displayed on the image display section 15 (Step S48). A reference image is an image of a normal semiconductor wafer that is free from any defect. As the reference image is displayed, the operation returns to the main menu.

Then, if the detected defect image display button is depressed (Step S49), it is determined if there is a detected defect image or not (Step S50). If it is determined that there is a detected defect image, it is displayed on the image display section image display section 15 (Step S51). As the detected defect image is displayed, the operation returns to the main menu.

Thus, as described above with an examination system 1 according to the invention, the parameter preparation support device 4 selects and/or alters the defect detection parameters and prepare classified defect image data for producing the knowledge base, it can support the operation of the automatic defect classification device 3 of detecting defect on semiconductors and hence the automatic defect classification device 3 can accurately detect defect on semiconductors. Additionally, since the automatic defect classification device 3 and the parameter preparation support device 4 are separated from each other in the examination system 1, the operation of preparing data on the isolated defective areas for the purpose of selecting and/or altering defect detection parameters and preparing the knowledge base can be conducted independently from the operation of classifying defects to improve the efficiency of the operation.

What is claimed is:

1. A semiconductor wafer examination system comprising:
    a defect classification device adapted to pick up an image of the surface (defect image) of a defective semiconductor wafer, compare the defect image with an image of the surface of a normal semiconductor wafer (normal image), identify each defective area isolated as characteristic area of a defect in the defect image on the basis of the outcome of the comparison and defect detection parameters for defining threshold value for defects and automatically determine the type of defect according to the characteristic quantity of the defective area on the basis of a knowledge base for determining the type of defect according to the characteristic quantity of the defective area; and
    a classification support device including
        a classification means for identifying the defective area of a plurality of defective images on the basis of the normal image and the defect detection parameters and classifying the identified defective areas,
        a defective area displaying means for displaying the plurality of defective areas as classified by said classification means,
        an editing means for editing the defect detection parameters on the basis of the defective areas displayed by said defective area display;
        said editing means including defect detection parameter read means for reading out from a defect parameter storage device, defect detection parameter selection means so as to select for all the defect parameters and defect detection parameter manual selection means so that values may be selected individually by the user on the basis of the defect detection parameter shown on the defective area display means,
        a classification result re-instruction editing means for manually re-classifying the result of classification of the defective areas obtained by said classification means, if the result of classification obtained by the detected defect classification means on the basis of the known knowledge base is wrong or the detected data can not be automatically classified by the detected defect classification means, and
        a manual selection means for selecting classified defect image data for preparing the knowledge base from the plurality of defective areas as classified by the classification result re-instruction editing means.

* * * * *